United States Patent [19]

Robinson

[11] 4,317,445

[45] Mar. 2, 1982

[54] CATHETER INSERTION UNIT WITH SEPARATE FLASHBACK INDICATION FOR THE CANNULA

[75] Inventor: Thomas P. Robinson, Plano, Tex.

[73] Assignee: Baxter Travenol Laboratories, Inc., Deerfield, Ill.

[21] Appl. No.: 136,082

[22] Filed: Mar. 31, 1980

[51] Int. Cl.³ .................. A61M 5/00; A61M 25/00
[52] U.S. Cl. ........................ 128/214.4; 128/349 R; 128/348; 128/DIG. 16
[58] Field of Search ............... 128/214.4, 214.2, 347, 128/348, 350 R, DIG. 16, 221, 349 R, DIG. 9

[56] References Cited

U.S. PATENT DOCUMENTS

| | | | |
|---|---|---|---|
| 3,097,646 | 7/1963 | Scislowicz | 128/221 |
| 3,219,036 | 11/1965 | Stafford | 128/214.4 |
| 3,459,188 | 8/1969 | Roberts | 128/347 |
| 3,500,828 | 3/1970 | Podhora | 128/214.4 |
| 3,515,137 | 6/1970 | Santomieri | 128/348 |
| 3,529,633 | 9/1970 | Vaillancourt | 128/214 |
| 3,547,119 | 12/1970 | Niles | 128/214.4 |
| 3,680,562 | 8/1972 | Wittes et al. | 128/214.4 |
| 3,860,006 | 1/1975 | Patel | 128/347 |
| 3,875,938 | 4/1975 | Mellor | 128/214.4 |
| 3,938,530 | 2/1976 | Santomieri | 128/349 R |
| 4,016,879 | 4/1977 | Mellor | 128/214.4 |
| 4,020,835 | 5/1977 | Nordstrom et al. | 128/214.4 |
| 4,046,144 | 9/1977 | McFarlane | 128/DIG. 16 |
| 4,073,297 | 2/1978 | Kopp | 128/214.4 |
| 4,180,068 | 12/1979 | Jacobsen et al. | 128/DIG. 16 |
| 4,193,399 | 3/1980 | Robinson | 128/214.4 |

Primary Examiner—Gene Mancene
Assistant Examiner—Michael J. Foycik
Attorney, Agent, or Firm—Richards, Harris & Medlock

[57] ABSTRACT

An intravenous assembly includes a needle extending through a hub and a catheter or cannula secured at its proximal end to the hub. The cannula includes a side port near the distal end thereof in fluid communication with an annular flashback chamber formed between the cannula and needle to provide visual indication of venous entry of the cannula. In another embodiment, a longitudinal slot in the internal wall of the cannula defines the cannula flashback chamber. In accordance with the preferred construction, the needle is hollow, and a plug is secured thereto defining another flashback chamber to provide a separate indication of venous entry of the needle.

11 Claims, 4 Drawing Figures

CATHETER INSERTION UNIT WITH SEPARATE FLASHBACK INDICATION FOR THE CANNULA

TECHNICAL FIELD

The present invention relates generally to an intravenous device. More particularly, this invention concerns an over-the-needle type of catheter insertion unit adapted to provide a separate flashback indication upon venous entry of the cannula.

BACKGROUND ART

Intravenous treatment and other medical infusion procedures require introduction of a flexible catheter into the vascular system of a patient. Catheters of the in-dwelling type are left in place between periodic uses to reduce the number of traumatic incidents to the patient which would otherwise occur if a separate puncture were required with each use. A popular form of such catheters is the so-called "over-the-needle" catheter which consists of a removable stylet needle extending through a cannula and a female fitting secured to the proximal end of the cannula. The needle serves to pierce the skin and blood vessel or fistula of the patient, simultaneously positioning the distal end of the cannula therein, after which the needle is removed and discarded. U.S. Pat. Nos. 3,456,006 and 3,714,945 show examples of this type of catheter insertion unit.

It has been common practice to provide such catheter insertion units with a flashback chamber in fluid communication with the hollow needle so that, upon blood vessel entry by the needle, blood could flow into the chamber and thereby provide a visual indication to the medical attendant. Of course, before withdrawal of the needle, the tip of the cannula should be positioned sufficiently within the blood vessel; however, blood flashback from the needle only indicates that the needle bevel has entered the blood vessel and does not necessarily mean that the cannula also has entered the blood vessel.

It is therefore desirable to provide a separate flashback capability to signal when the cannula has entered the blood vessel. Needle flashback without cannula flashback would indicate that the cannula or whole unit should be inserted further. The occurrence of cannula flashback before or after needle flashback would indicate that no further insertion of the needle is necessary, thereby facilitating the accuracy of the procedure, minimizing discomfort to the patient, and reducing or eliminating damage to the blood vessel.

The catheter insertion units of the prior art, however, either have lacked this feature entirely, have been of unnecessarily complex and therefore costly construction or have suffered from other disadvantages. Although provision of side ports in the cannula to facilitate fluid flow is well known in the art, the catheter insertion units heretofore have been constructed to block the side ports before withdrawal of the needle, and have lacked any provision for a separate chamber in communication with the side ports for indicating cannula entry before removal of the needle. Moreover, even if separate chambers in fluid communication with the side ports were provided in the prior devices, the sideports have not been located sufficiently close to the distal catheter tip for flashback when the cannula entered a blood vessel.

A need has thus arisen for a simplified catheter insertion unit which provides an independent flashback indication of cannula entry into a blood vessel before removal of the needle.

SUMMARY OF THE INVENTION

The present invention comprises a catheter insertion unit of the over-the-needle type which overcomes the foregoing and other difficulties associated with the prior art. In accordance with the invention, a small deadspace or chamber ported to the outside of the cannula is defined between the cannula and the needle to provide a separate blood flashback indication when the cannula enters the blood vessel, thereby facilitating introduction of the catheter and reducing the possibility of unnecessary discomfort to the patient from overinsertion.

More particularly, the present invention comprises a catheter insertion unit having a removable needle extending within a cannula and a female fitting secured to the proximal end of the cannula. The needle can be hollow or solid, and structure defining a vented flashback chamber is secured to the proximal end of the needle to provide a visual indication of venous entry of the needle. At least one side port is formed in the distal end of the cannula, and a small deadspace or flashback chamber is provided between the cannula and the needle to provide a visual indication of veinous entry of the cannula. In one embodiment, the cannula flashback chamber is defined by an enlarged internal diameter portion of the cannula which surrounds the needle and extends from the side port toward the fitting. In another embodiment, the cannula flashback chamber is defined by a longitudinal slot in the internal wall of the cannula.

BRIEF DESCRIPTION OF DRAWINGS

A more complete understanding of the invention can be had by reference to the following Detailed Description in conjunction with the accompanying Drawings, wherein.

DETAILED DESCRIPTION

Figure 1:
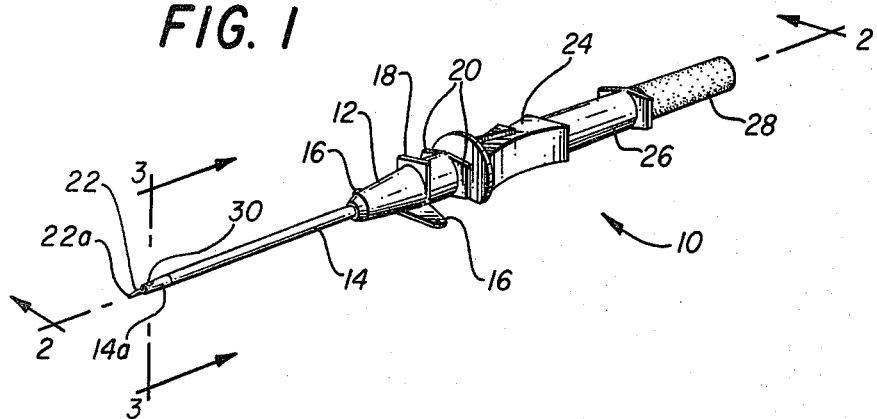
FIG. 1 is a perspective view of a catheter insertion unit incorporating the invention.

Referring now to the Drawings wherein like reference numerals designate like or corresponding parts throughout the views, and particularly referring to FIG. 1, there is shown a catheter insertion unit 10 incorporating the invention. Insertion unit 10 includes a female hub 12 which can be formed of plastic or other suitable material. A flexible catheter tube or cannula 14 is secured at its proximal end to hub 12 and extends forwardly therefrom. Cannula 14 is formed from suitable transparent or translucent radiopaque synthetic material, such as polyvinyl, polypropylene, polyethylene, polytetrafluoroethylene, or the like.

Integral projections are provided on hub 12 to facilitate attachment to a patient or connection of infusion devices to the hub. A pair of wings 16 are preferably provided to facilitate attachment to the patient by means of tape, sutures, or the like. Hub 12 also includes an ear 18 and a pair of flanges 20 for engagement with locking dogs on an obturator or another infusion device, such as a syringe.

Catheter insertion unit 10 further includes a removable stylet needle 22 extending through hub 12 and cannula 14. The distal end 22a of needle 22 is beveled to facilitate insertion, and protudes beyond the distal end 14a of cannula 14. In the preferred embodiment, needle 22 is hollow, however, a solid needle could be used, if desired. A hub 24, which may be formed of plastic or other suitable material, is secured to the proximal end of needle 22 in fluid communication therewith. The distal end of hub 24 defines a nose which seats within fitting 12. The proximal end of hub 24 defines a vented flashback chamber 26 into which blood flows upon veinous entry of needle 22. Flashback chamber 26 is closed by a semipermeable plug 28 which allows air to flow from the chamber while preventing the flow of blood therefrom. For example, a self-venting plug like that shown in application Ser. No. 813,890, now U.S. Pat. No. 4,193,399, assigned to the assignee hereof, may be used for plug 28.

A side port 30 is located in cannula 14 as closely adjacent to the distal end 14a as is practical. Side port 30 can be, for example, 3 to 5 mils in diameter, or sufficiently large to permit bloodflow therethrough. Catheter insertion unit 10 includes at least one side port 30 in cannula 14, however, multiple side ports therein can be provided, if desired. It will be understood that the provision of a side port 30 through the wall of cannula 14 comprises a significant feature of the present invention, as will be more fully explained hereinafter.

Figure 2:
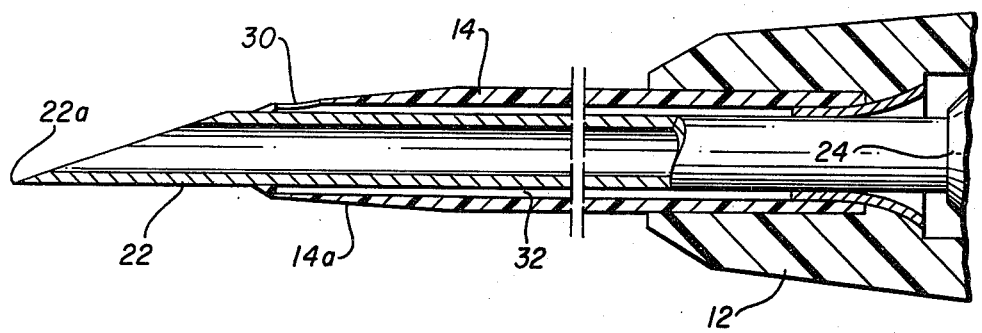
FIG. 2 is an enlarged partial sectional view taken generally along lines 2—2 of FIG. 1 in the direction of the arrows.
Figure 3:
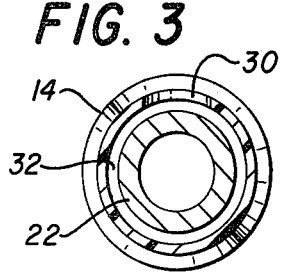
FIG. 3 is an enlarged sectional view taken along lines 3—3 of FIG. 1 in the direction of the arrows.

Further constructional details of the present invention are shown in FIGS. 2 and 3. The distal end 14a of cannula 14 forms a close-fitting, fluid-tight seal about needle 22. Side port 30 extends through cannula 14 and opens onto an annular chamber or annulus formed between the cannula and needle 22. Annulus 32 can be, for example, about 5 to 10 mils in width, and preferably extends from side port 30 to fitting 12. Annulus 32 thus defines a deadspace between cannula 14 and needle 22 into which blood can flow via side port 30 when the tip of the cannula enters a blood vessel, thereby providing a separate and independent visual indication of cannula entry. Of course, venous entry of needle 22 would be signaled first by bloodflow through the lumen of the needle and into flashback chamber 26.

Figure 4:
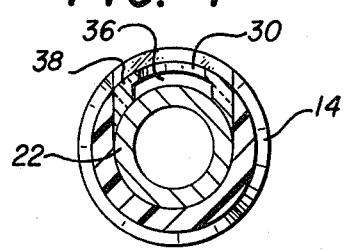
FIG. 4 is an enlarged sectional view of an alternate embodiment.

FIG. 4 illustrates an alternate embodiment of the invention. A longitudinal slot 36 defining a deadspace between cannula 14 and needle 22 can be formed in the internal wall of the cannula in place of the annular chamber 32 shown in FIGS. 2 and 3. Slot 36 is located on the top side of cannula 14 and extends from side port 30 toward fitting 12 and preferably all the way to the the slot should be sufficiently deep to allow bloodflow therethrough. For example, slot 36 can be about 15 to 20 mils in depth. Cannula 14 can comprise either a translucent section of radiopaque tubing, or a section of window-wall tubing having a substantially transparent strip 38 extruded therein to serve as the site for slot 36. For instance, such window-wall tubing is commercially available from Martech Corporation of Lansdale, Pa. In all other respects, a catheter insertion unit incorporating a slot 36 in the internal wall of cannula 14 would function like one having a counterbored cannula to provide a visual indication by means of blood flashback upon venous entry of the cannula.

In view of the foregoing, it will thus be understood that the present invention comprises an improved catheter insertion unit having several advantages over the prior art. The invention provides a direct and independent visual flashback indication of venous entry of the catheter, as opposed to venous entry of the piercing needle, to enhance accuracy of the venapuncture procedure. Other advantages of the invention will suggest themselves to those skilled in the art.

Although particular embodiments of the invention have been illustrated in the accompanying Drawings and described in the foregoing Detailed Description, it will be understood that the invention is not limited to the embodiments disclosed, but is intended to embrace any alternatives, equivalents, and rearrangements or substitutions of elements as fall within the scope of the invention as defined by the following claims.

I claim:

1. In an intravenous unit of the type having a catheter secured at its proximal end to a hub, and a removable piercing needle extending through the hub and catheter with the tip of the needle protruding beyond the distal end of the catheter, the improvement which comprises:

said catheter having internal and external surfaces;
said catheter including a side port therein located adjacent to the distal end of said catheter; and
the internal surface of said catheter around the side port being configured to define a predetermined flashback chamber between said catheter and needle and extending from the side port to the hub for providing a visual indication of venous entry of said catheter.

2. The intravenous unit of claim 1, wherein the flashback chamber comprises an annulus surrounding said needle and extending from the side port to said hub.

3. The intravenous unit of claim 1, wherein the flashback chamber comprises a longitudinal slot extending from the side port to said hub.

4. An intravenous assembly, comprising:

a cannula having distal and proximal ends, and internal and external surfaces;
a hub secured to the proximal end of said cannula, said hub defining a female fitting in fluid communication with said cannula;
a needle extending through said cannula and hub;
said needle having a distal pointed end protruding beyond the distal end of said cannula and a proximal end extending into said hub;
said cannula including a side port located near the distal end thereof;
the internal surface of said cannula around the side port being configured to define a predetermined first flashback chamber extending from the side port to the hub for providing a visual indication of venous entry of said cannula; and
a plug secured to the proximal end of said needle, said plug defining a male fitting removably seated in said hub.

5. The intravenous assembly of claim 4, wherein the first flashback chamber comprises an annulus surrounding said needle and extending from the side port to said hub.

6. The intravenous assembly of claim 4, wherein the first flashback chamber comprises a longitudinal slot extending from the side port to said hub.

7. The intravenous assembly of claim 4, wherein said needle is hollow, and further including:

structure defining a second flashback chamber secured to said plug in fluid communication with said needle for providing a visual indication of veinous entry of said needle.

8. An intravenous assembly, which comprises:

a cannula having distal and proximal ends, and internal and external surfaces;

a hub secured to the proximal end of said cannula, said hub defining a female fitting in fluid communication with said cannula;

a hollow needle extending through said cannula and hub;

said needle having a distal pointed end protruding beyond the distal end of said cannula, and a proximal end extending into said hub;

said cannula including a side port therein located proximate the distal end of said cannula;

the internal surface of said cannula around the side port being configured to defined a predetermined first flashback chamber between said cannula and needle and extending from the side port to the hub for providing a visual indication of venous entry of said cannula;

a plug secured to the proximal end of said needle, said plug defining a male fitting removably seated in said hub; and structure defining a predetermined second flashback chamber secured to said plug in fluid communication with said needle for providing another visual indication of venous entry of said needle.

9. The intravenous assembly of claim 8, wherein the first flashback chamber comprises an annulus of predetermined width surrounding said needle and extending from the side port toward said hub.

10. The intravenous assembly of claim 8, wherein the first flashback chamber comprises a longitudinal slot of predetermined depth extending from the side port towards said hub.

11. The intravenous assembly of claim 8, wherein said second flashback chamber includes a port for venting said chamber to atmosphere, and further including:

means located in the port of said second flashback chamber for permitting venting of air from said chamber while substantially preventing blood flow therefrom.

* * * * *